United States Patent
Schenker et al.

(10) Patent No.: US 12,067,685 B2
(45) Date of Patent: Aug. 20, 2024

(54) ELECTRONIC TREATMENT DEVICE

(71) Applicant: Mind Switch AG, Baar (CH)

(72) Inventors: Michaela Schenker, Zufikon (CH); Andre Schenker, Zufikon (CH)

(73) Assignee: MIND SWITCH, AG, Baar (CH)

( * ) Notice: Subject to any disclaimer, the term of this patent is extended or adjusted under 35 U.S.C. 154(b) by 208 days.

(21) Appl. No.: 17/876,961

(22) Filed: Jul. 29, 2022

(65) Prior Publication Data
US 2023/0274505 A1    Aug. 31, 2023

(51) Int. Cl.
*G06T 19/00* (2011.01)
*G06F 3/01* (2006.01)

(52) U.S. Cl.
CPC ............ *G06T 19/006* (2013.01); *G06F 3/017* (2013.01); *G06T 2200/24* (2013.01)

(58) Field of Classification Search
None
See application file for complete search history.

(56) References Cited

U.S. PATENT DOCUMENTS

| | | | | |
|---|---|---|---|---|
| 10,758,780 | B2 * | 9/2020 | Putnam | A61B 5/6891 |
| 2010/0097322 | A1 * | 4/2010 | Hu | G06F 3/04883 345/173 |
| 2011/0027765 | A1 | 2/2011 | Nader | |
| 2011/0320049 | A1 * | 12/2011 | Chossat | G16H 20/17 700/285 |
| 2013/0141697 | A1 * | 6/2013 | Berry | G16H 10/60 351/242 |
| 2013/0239058 | A1 * | 9/2013 | Yao | H04M 1/67 715/833 |
| 2013/0332856 | A1 * | 12/2013 | Sanders | G06F 3/0488 715/753 |

(Continued)

Primary Examiner — Kyle Zhai
(74) Attorney, Agent, or Firm — Donald J. Ersler (57) ABSTRACT

An electronic apparatus (1) configured to provide a treatment for a psychological anxiety disorder, the electronic apparatus including: a memory storing at least one instruction; a user interface (13) including a display configured to display a plurality of images; and a processor (11). The processor, by executing the at least one instruction, is configured to: based on a first user input received through the user interface (13), generate a first dynamic image including an expanding graphical element among the plurality of images, and render the first dynamic image on the display (14) such that an expansion is centered on a point located in a central region of the display (14), generate a graphical turning element which is rendered on the display in a first state and subsequently rendered on the display in a second state different from the first state, among the plurality of images, render, on the display, a full-body image of a user in a pre-defined orientation, a pre-defined location, and a pre-defined size, among the plurality of images generate a graphical switch element which is rendered on the display in a first state and subsequently rendered on the display in a different second state, among the plurality of images, and generate a second dynamic image including a contracting graphical element among the plurality of images, and render the second dynamic image on the display (14) such that a contraction is centered on the point located in the central region of the display (14).

13 Claims, 9 Drawing Sheets

(56) References Cited

U.S. PATENT DOCUMENTS

| | | | | |
|---|---|---|---|---|
| 2018/0174366 A1* | 6/2018 | Nishibe | .................... | G06F 3/013 |
| 2019/0196210 A1* | 6/2019 | Umemori | ................ | G09F 19/14 |
| 2019/0246890 A1* | 8/2019 | Kerasidis | ............. | A61B 3/0008 |
| 2021/0027513 A1* | 1/2021 | Choi | ..................... | G06T 15/205 |
| 2022/0198780 A1* | 6/2022 | Doba | .................... | G06F 16/538 |
| 2023/0112728 A1* | 4/2023 | Yoo | ........................ | G16H 20/70 |
| 2023/0188830 A1* | 6/2023 | Chen | ................... | H04N 23/667 |
| | | | | 348/207.99 |

* cited by examiner

SOMATOSENSORY – MOTOR CORTEX

ELECTRONIC TREATMENT DEVICE

FIELD OF THE DISCLOSURE

The present disclosure relates to an electronic apparatus configured as a treatment device.

BACKGROUND OF THE DISCLOSURE

There is a wide range of psychological anxiety disorders, which includes panic disorders, phobias, generalized anxiety disorder, and separation anxiety. Other related mental health conditions share some features with anxiety disorders, including post-traumatic stress disorder and obsessive-compulsive disorder. Further, in many stressful everyday situations there are latent fears which play a role, for example, the fear of failure, the fear of not being good enough, or the fear of not belonging. Ultimately, much of what stresses people is the result of a fear.

There are many specific phobias, such as acrophobia (fear of heights), agoraphobia (fear of public places), and claustrophobia (fear of closed-in places). Other phobias result in people becoming anxious and very self-conscious in social situations, for example meeting new people. Other common phobias involve animals (such as spiders), tunnels, flying, driving, water, blood, and injections. Such anxiety disorders are typically treated in a clinical setting, with each person having their particular form of anxiety disorder treated by a treatment professional, for example a psychiatrist or psychotherapist. Psychotherapeutical approaches include cognitive behavioral therapy and exposure therapy. Along with psychotherapy, medication (for example anti-anxiety medications, antidepressants, and beta-blockers) may also be prescribed.

Several devices and methods are known for treatments which help overcome various disorders such as stress, fear and anxiety. These devices require supervision, set up and/or instruction by a treatment professional and/or user interaction during the treatment as disclosed in US 2011/0027765 A1. For many people with these issues, especially if the impact on their daily lives is limited to few occasions, the effort to involve a treatment professional is too high and/or they feel there is shame in seeking such treatment. In addition user interaction during a treatment can further increase stress and may be incorrect due to the immediate state of the user.

SUMMARY OF THE DISCLOSURE

It is an object of embodiments disclosed herein to provide an electronic treatment device, in particular configured to provide a treatment for a psychological anxiety disorder, specifically fears and phobias, and other sources of stress. Another object of the invention is to provide a simple and flexible device for autonomous use according to the users individual needs.

In particular, it is an object of embodiments disclosed herein to provide an electronic treatment device configured to provide a treatment for a psychological anxiety disorder. The electronic apparatus includes a memory storing at least one instruction, a processor and a user interface. The user interface comprises a display configured to display a plurality of images. The processor is configured to, by executing the at least one instruction, receive a first user input through the user interface. The processor is configured to generate a first dynamic image comprising an expanding graphical element. The expanding graphical element is among the plurality of images. The processor is configured to render the first dynamic image such that the expansion is centered on a point located in a central region of the display. The processor is configured to generate a graphical turning element which is rendered on the display, among the plurality of images, by the processor in a first state and subsequently rendered on the display by the processor in a second state. The processor is configured to render, on the display, a full-body image of a user in a pre-defined orientation, a pre-defined location, and a pre-defined size, among the plurality of images. The processor is configured to generate a graphical switch element which is rendered on the display by the processor in a first state and subsequently rendered on the display by the processor in a different second state, among the plurality of images. The processor is configured to generate a second dynamic image comprising a contracting graphical element, wherein the second dynamic image is rendered on the display by the processor such that the contraction is centered on the point located in the central region of the display.

A scientific study was performed to evaluate the efficacy of the disclosed electronic apparatus when used to treat individuals suffering from arachnophobia. The scientific study found a significant reduction not only in self-reported levels of stress when viewing images of spiders as opposed to control images, but functional magnetic resonance imaging (FMRI) showed a significant reduction in activity in the amygdala, the bilateral visual cortex, and the somatosensory—motor cortex after treatment. The scientific study is explained in more detail below.

In an embodiment, the first dynamic image is generated by the processor such that it further includes one or more first moving graphical elements, wherein each of the one or more moving graphical elements moves outwards from the point located in the central region of the display.

In an embodiment, the second dynamic image is generated by the processor such that it further includes one or more second moving graphical elements, wherein each of the second moving graphical elements moves outwards from the point located in the central region of the display.

In an embodiment, the display is split into quadrants and the processor is further configured to generate a sequence of point-like graphical elements rendered to appear and disappear individually at a plurality of positions on the display, such that at least one point-like graphical element appears in each quadrant of the display.

In an embodiment, at least one from among the first dynamic image and/or the second dynamic image is generated having a black background and at least one from among the expanding graphical element and/or the contracting graphical element has a white color.

In an embodiment, the processor is configured to perform image processing on the full-body image of the user such that it is rendered by the processor as a desaturated full-body image, and wherein the desaturated full-body image has a size in a lengthwise direction between 3 cm to 8 cm tall on the display, preferably 5 cm. In an embodiment, the full-body image of the user is rendered as a partially transparent full-body image.

In an embodiment, the processor is configured to render the graphical switching element and/or the graphical turning element overlaid on the full-body image. For example, the processor is configured to render the turning element prior to rendering the full-body image of the user.

In an embodiment, the processor is configured to generate and render one or more of: the full-body image, the graphical turning element, or the graphical switch element, such that they are rendered for a pre-determined period of time and then fade, at a pre-determined fade rate.

In an embodiment, the processor is configured to generate the second state of the graphical turning element such that it corresponds to a rotated first state of the graphical turning element by an angle of 180°.

In an embodiment, the processor is configured to receive, from the user interface, the user input including an indication of one or more types of psychological anxiety disorder.

In an embodiment, the processor is configured to receive, from the user interface, a first user input including an indication of a first stress level of the user, prior to rendering the first dynamic image. The processor is configured to receive, from the user interface, a second user input including an indication of a second stress level of the user, subsequent to rendering the second dynamic image. In an further example the processor is configured to determine whether the stress level of the user has reduced by comparing the second stress level to the first stress level.

In an embodiment, the apparatus includes a speaker, wherein the processor is configured to play back one or more audio tracks associated with the rendered images, the audio tracks conveying instructions to the user.

In an embodiment, the electronic apparatus is a portable communications device, for example a smart phone, a tablet computer, a smart watch, or a laptop.

In an embodiment, the display of the user interface includes an augmented reality display and/or a virtual reality display.

In addition to an electronic apparatus, the present disclosure also relates to a computer program product including a non-transitory computer-readable medium having stored thereon computer program code for controlling a processor of an electronic apparatus having a user interface with a display to generate a first dynamic image including an expanding graphical element, wherein the first dynamic image is rendered on the display such that the expansion is centered on a point located in a central region of the display. The computer program code controls the processor to generate a graphical turning element which is rendered on the display in a first state and subsequently rendered on the display in a second state. The computer program code controls the processor to render, on the display, a full-body image of a user in a pre-defined orientation, location, and size. The computer program code controls the processor to generate a graphical switch element which is rendered on the display in a first state and subsequently rendered on the display in a second state. The computer program code controls the processor to generate a second dynamic image including a contracting graphical element, which second dynamic image is rendered on the display such that the contraction is centered on the point located in the central region of the display.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DESCRIPTION OF THE EMBODIMENTS

Reference will now be made in detail to certain embodiments, examples of which are illustrated in the accompanying drawings, in which some, but not all features are shown. Indeed, embodiments disclosed herein may be embodied in many different forms and should not be construed as limited to the embodiments set forth herein; rather, these embodiments are provided so that this disclosure will satisfy applicable legal requirements. Whenever possible, like reference numbers will be used to refer to like components or parts.

Figure 1:
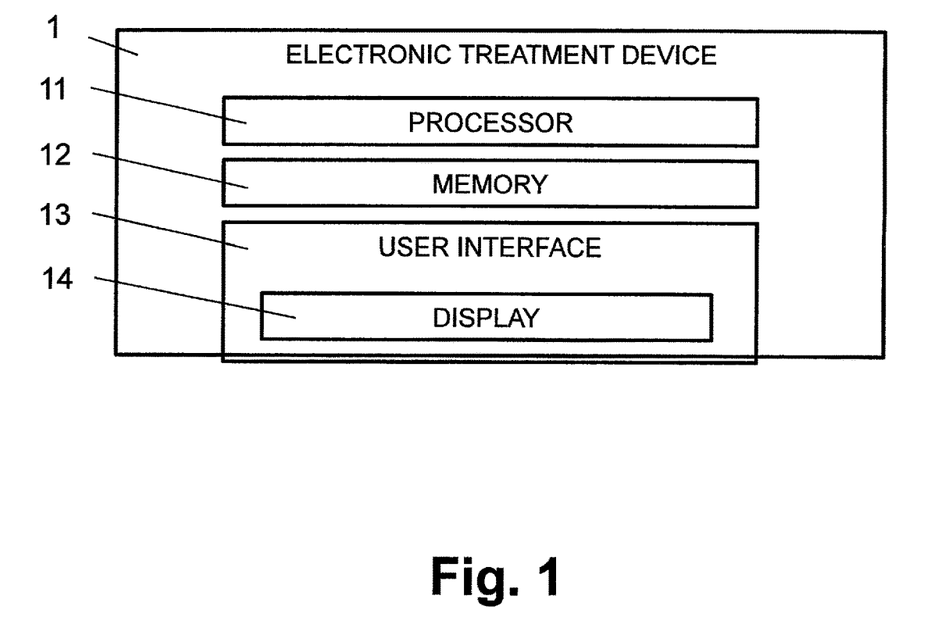
FIG. 1 shows a block diagram illustrating schematically an electronic treatment device.

FIG. 1 shows a block diagram illustrating schematically an electronic treatment device 1, e.g., an electronic apparatus. The electronic treatment device 1 is a computerized device used by a user having a psychological anxiety disorder, for example a phobia, a panic disorder, but also other types of fear or stress. The electronic treatment device 1 includes one or more processors 11, a memory 12, and a user interface 13. Optionally, the electronic treatment device 1 includes a communication interface and other hardware modules, for example a speaker. The processors 11 include one or more central processing units (CPUs) and/or other programmable circuits or logic units such as ASICs (Application-Specific Integrated Circuits), for example GPUs (graphics processing units). The memory 12 includes volatile and/or non-volatile memory, e.g., random-access memory and/or flash memory having stored thereon program code and data. The program code is configured to control the processors 11, in particular to perform one or more of the steps and/or functions described herein. The data stored on the memory 12 includes user data, in particular a full-body image 2 of the user.

In an embodiment, the program code is implemented as a software application which is installed on the electronic treatment device 1. For example, the software application is downloaded from a remote server and installed on the electronic treatment device 1. In another example, the software application is downloaded from a portable data carrier, such as a CD-ROM or a USB device, and installed on the electronic treatment device 1.

In another embodiment, the program code is implemented as a web application which is loaded from a remote server and executed on the electronic treatment device 1 using a web browser.

The communication interface is further configured for data communication with one or more external devices. For example, the communication interface includes a network communications interface, for example an Ethernet interface, a WLAN interface, and/or a wireless radio network interface for wireless and/or wired data communication using one or more networks, including, for example, a local network such as a LAN (local area network), and/or the Internet.

The skilled person is aware that at least some of the steps and/or functions described herein as being performed on the processor 11 of the electronic treatment device 1 may be performed on one or more auxiliary processing devices connected to the processor 11 of the electronic treatment device 1 using the communication interface. The auxiliary processing devices can be co-located with the electronic treatment device 1 or located remotely, for example on an external device, such as a remote server computer (e.g., a cloud-based server).

The skilled person is also aware that at least some of the program code (e.g., application data) or data (e.g., user data associated with a particular user), and described as being stored in the memory 12 of the electronic treatment device 1 may be stored on one or more auxiliary storage devices connected to the electronic treatment device 1 using the communication interface.

The user interface includes a display. The display is, for example, a flat-panel display such as an LCD or OLED screen, optionally having a touch-interface for recording user input. The user interface further includes, depending on the embodiment, one or more user input devices, such as a keyboard or a touch screen. The user interface is configured to receive user inputs from the user, in particular based on, or in response to, information displayed to the user using the one or more output devices.

Depending on the embodiment, the electronic treatment device 1 is implemented as, or includes, a personal computer, for example a desktop computer, a laptop computer, a tablet computer, or a smart phone.

In an embodiment, the display 14 of the electronic treatment device 1 includes a virtual reality (VR) display, augmented reality (AR) display, and/or mixed reality display. The graphical elements, images, and other visual objects and/or effects described herein as being displayed on the display 14 correspond to graphical elements, images, and other visual objects and/or effects displayed within the context of a VR, AR, and/or mixed reality environment. Depending on the embodiment, this includes generating and/or rendering some of the aforementioned at a different size or location in relation to the user than described herein.

In an embodiment, the full-body image 2 of the user is a three-dimensional image of the user. The three-dimensional image of the user is generated, for example, from a series of still images, such as from a stereoscopic camera.

In an embodiment, the full-body image 2 of the user includes a number of visual attributes, at least one computer-generated visual attribute. The visual attributes include clothing, facial expression, direction of gaze, and posture.

In an embodiment, the electronic treatment device 1 includes a camera. The camera is used by the user to record a full-body image of the user, for use in the treatment as described herein.

Figure 2:
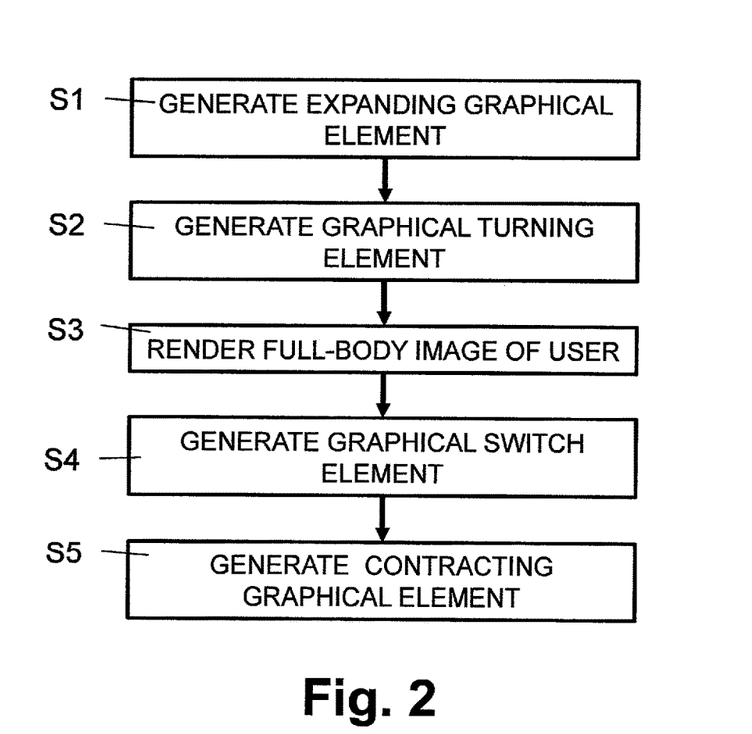
FIG. 2 shows a flow diagram illustrating an exemplary sequence of steps performed by the electronic treatment device.

FIG. 2 shows a flow diagram illustrating an exemplary sequence of steps for carrying out the invention. The sequence of steps described herein have the effect of reducing the anxiety and fear that the user has when confronted with, or contemplating, a source of the user's fear or phobia. As is described below in more detail (in particular with reference to FIGS. 9 and 10), the user is initially required to select a particular phobia or a fear by interacting with the user interface 13 of the electronic treatment device 1. The user additionally may select a particular aspect of that phobia or fear which the user wishes to address. The below described steps are then performed by the electronic treatment device 1 while the user contemplates and reflects on the user's phobia, fear, or source of stress, for example the particular aspect of the user's phobia, fear, or source of stress. A single run through the collection of steps described herein may last from between 30 seconds to 10 minutes, for example approximately 90 seconds. A given treatment session may include of multiple runs through the collection (for example, up to 100 runs, in particular between 20-60 runs). The user may also select, for different runs through the collection, different aspects of the particular fear or phobia which the user wishes to address. Depending on the user and the particular phobia or fear, multiple treatment sessions may be necessary to achieve a reduction in stress.

The particular collection of steps below has been developed through extensive experimentation and study by the Applicant. The steps have been shown in a study (discussed herein in detail) to significantly reduce the stress associated with the particular fear or phobia over time. As is demonstrated in the study, the stress reduction is a result of a change in the brain activity of several regions of the brain as a result of the particular visual stimuli supplied by the electronic treatment device 1 and the produced physiological effects, in particular by aiding the user in changing the user's self-image.

In step S1, the processor 11 is configured to render an expanding graphical element 31*a* (as is described in more detail with reference to FIGS. 3*a* and 3*b*) as part of a first dynamic image. In a preferred embodiment the first dynamic image is displayed for 5-60 seconds depending on the type of graphical element. Preferably, the expanding graphical element is rendered for a first period (5-30 seconds) as part of the first dynamic image, and after this period has elapsed an end-state of the expanding graphical element (i.e. a static image of the expanding graphical element after it has finished expanding) is rendered for a second period of time (0-30 seconds). The expanding graphical element 31*a* is rendered on the display 14 and represents and/or invokes in the user imagery associated with entering a space filled with light. This has the effect of focusing the mind of the user and drawing the user's attention towards the center of the display 14. The user focuses on a particular aspect of a particular phobia, fear, or stress. The expanding graphical element 31*a* aids the user in the user's focusing as the user withdraws from the outside world to focus on the particular aspect. Thereby, specific locations in the brain responsible for the fact that this aspect is interpreted by the brain as a source of stress are addressed.

In an embodiment, a plurality of moving graphical elements 32a are generated, by the processor 11, and rendered on the display 14, as moving outwards (as is described in more detail with reference to FIG. 4a). In particular, the moving graphical elements 32a are generated as small or point-like moving graphical elements 32a which are rendered to move outwards from a central region of the display 14. The outwardly moving graphical elements 32a have the effect of invoking movement, such that the user feels as though the user is moving towards the central region of the display 14, feeling as though the moving graphical elements 32a are rushing past the user. Depending on the embodiment, the moving graphical elements 32a are rendered prior to rendering the expanding graphical element 31a, rendered simultaneously with the expanding graphical element 31a as part of the first dynamic image, and/or rendered subsequent to rendering the expanding graphical element 31a as described in step S1. These moving graphical elements 32a aid in focusing the user's attention on the particular aspect of the user's phobia, fear, or source of stress.

Figure 5A:
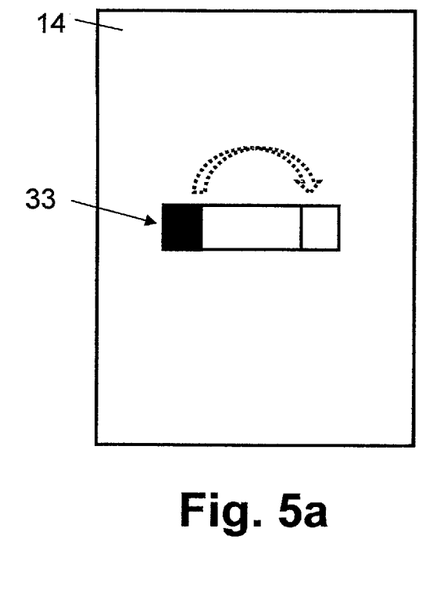
FIGS. 5a and 5b show illustration of a display showing a turning element.
Figure 5B:
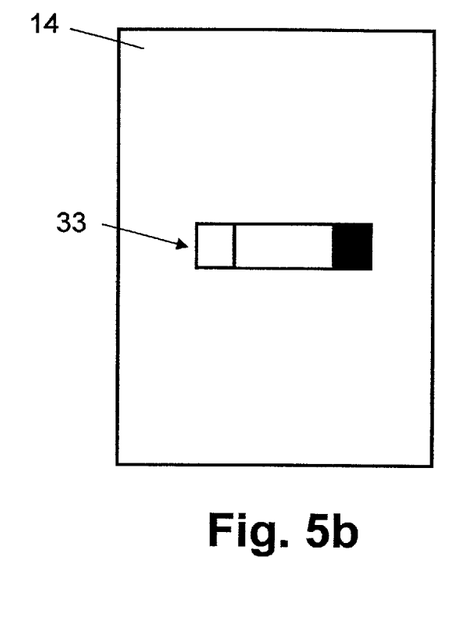

In step S2, a graphical turning element 33 is generated by the processor 11. The graphical turning element 33 is generated such that it has an axis of asymmetry, such that the graphical turning element 33 appears differently when rotated, in particular when rotated about 180 degrees. For example, the graphical turning element 33 is generated to appear, when rendered, as a battery with a positive and a negative pole. Alternatively, the graphical turning element 33 is generated to appear, when rendered, as an arrow. An example of a graphical turning element 33 is shown in FIGS. 5a and 5b. The graphical turning element 33 is rendered on the display by the processor 11. The graphical turning element 33 is generated to take 1-10 seconds to turn, preferably 5 seconds. The imagery of a graphical turning element 33 aids the user in overcoming internal mental blocks, in particular unconscious mental blocks. The graphical turning element 33 removes or disarms these mental blocks and enables a change to take place in the mind of the user.

In an embodiment, the processor 11 is configured to receive, from the user via the user interface 13, a user input (for example a touch input or a gesture input through the touch display 14), and to rotate the graphical turning element 33 depending on the user input. This interactivity improves the effect of disarming the mental blocks.

In step S3, a full-body image 2 of the user is rendered on the display 14 by the processor 11. The full-body image 2 is retrieved from the memory 12 and, in an embodiment, is an image the user recorded using a camera of the electronic treatment device 1. The full-body image 2 is for example processed, by the processor 11, such that it is desaturated (e.g. it appears in in gray-scale or black and white). The full-body image 2 is for example generated such that it appears, when rendered, to be partially transparent. Alternatively or additionally, the full-body image 2 is rendered such that it appears surrounded by fog. In a preferred embodiment the full-body image 2 is rendered, for 5-60 seconds, preferably 10 seconds. After rendering the full-body image 2, the processor is configured, not to render any particular image for 5-10 seconds, preferably 6 seconds. By rendering the full-body image 2, the user sees the user's image not as a literal and highly accurate photograph, but sees in the full-body image 2 a symbolic representation of the user. This makes it possible for the user to engage with the user's self-image and effect a change in this self-image, in particular in removing a false association with the particular aspect of the user's phobia, fear, or source of stress, and a fearful and/or stressful reaction.

In an embodiment, instead of the full-body image 2, an image of only part of the body of the user is used, for example a facial image of the user.

Figure 6A:
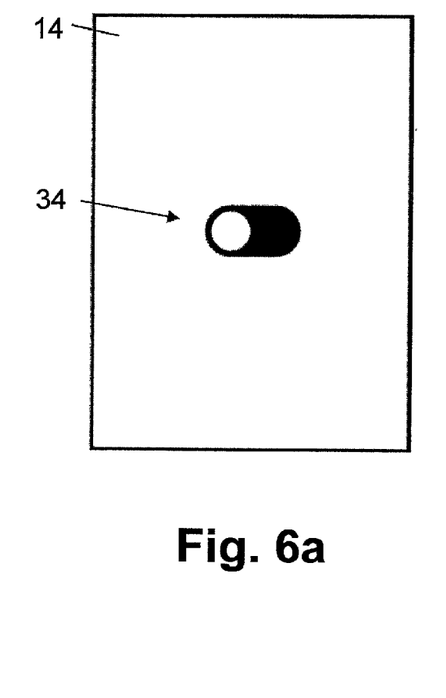
FIGS. 6a and 6b show illustration of a display showing a switching element.
Figure 6B:
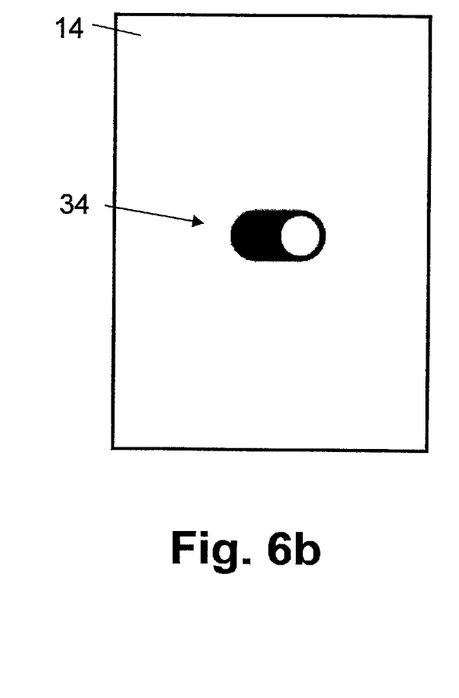

In step S4, a graphical switch element 34 is generated by the processor 11 and rendered on the display 14. The graphical switch element 34 is, for example, generated such that it appears as a slide-switch, a lock, or a light-switch. An example of the graphical switch element 34 is shown in FIGS. 6a and 6b. The graphical switch element 34 is generated and rendered by the processor 11 such that it switches from a first state to a different second state. In a preferred embodiment the graphical switch element 34 is configured to appear subsequent to the full-body image 2 0-10 seconds later, preferably 6 seconds later. The image of the graphical switch element 34 switching from the first state to the second state further aids the user in unlocking the user's established stress reaction to the particular aspect of the user's phobia, fear, or source of stress, and making it amenable to change.

In an embodiment, the processor 11 is configured to receive from the user, via the user interface 13, a user input (for example, a swipe gesture on a touch display 14), and to switch the graphical switch element 34 from the first state to the second state depending on the user input. The interactivity further aids the user in unlocking the user's established stress reaction.

In an embodiment, the change of state is accompanied by an audio signal, in particular a clear tone, generated by the processor 11 and played back via a speaker, for example a speaker of the electronic treatment device.

In an embodiment, the graphical switch element 34 is generated such that it is partially transparent and rendered overlaid on the full-body image 2 of the user. The overlay of the graphical switch element 34 over the full-body image 2 of the user further aids the effect of unlocking the user's mind and enabling a change to take place. In a preferred embodiment the graphical switch element 34 is rendered subsequent to the full-body image 2 appearing 0-10 seconds later, preferably 6 seconds later, after which the graphical switch element 34 and the full-body image 2 are rendered overlaid. The graphical switch element 34 and the full-body image 2 are then rendered for 2 to 10 seconds, preferably 4 seconds. Preferably, the graphical switch element 34 and the full-body image 2 then disappear simultaneously.

In an embodiment where the electronic treatment device 1 is a smart-phone, the full-body image 2 is generated such that it is rendered at a pre-defined size on the display 14, for example rendered to have a size of 3 cm to 8 cm tall on the display (14), most preferably 5 cm. The rendered size of the full-body image 2 is dependent on the size of the display 14 and a distance between the display 14 and the user.

In an embodiment where the display 14 includes a VR, AR, or mixed-reality display, the full-body image 2 is generated and rendered to be the same size as the user and at a distance of between 3 meters and 10 meters away from the user, for example 5 meters away. For example, the full-body image 2 is rendered three-dimensionally, for example using a three-dimensional full-body image, or by generating a three-dimensional avatar whose appearance matches that of the full-body image 2 of the user.

Figure 7A:
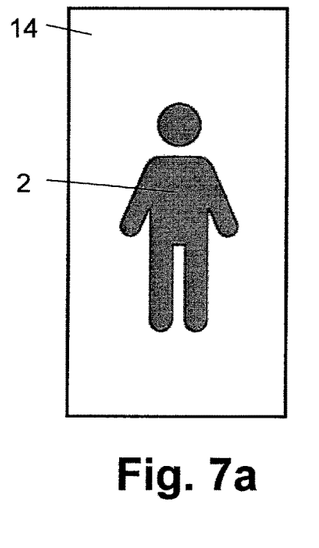
FIGS. 7a, 7b, and 7c show illustration of a display showing a full-body user image.
Figure 7B:
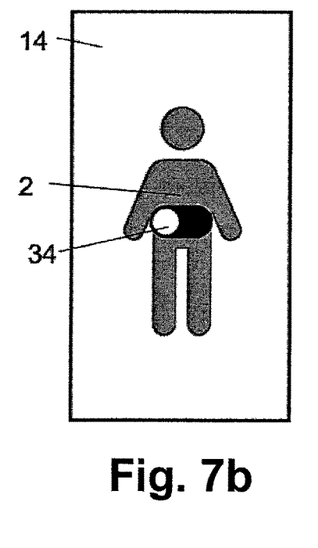
Figure 7C:
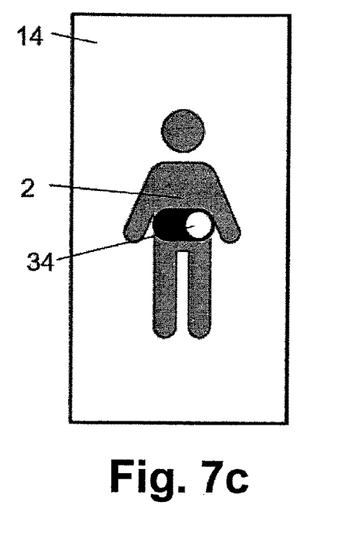

In an embodiment, the full-body image 2 of the user is generated and rendered such that it gradually appears. An example of the full-body image 2 is shown in FIGS. 7a to 7c.

Depending on the embodiment, the full-body image 2 of the user is displayed prior to, simultaneously with, or subsequent to the graphical switch element 34. For example, the graphical switch element 34 is rendered on top of the full-body image 2 of the user. The processor 11 is configured to switch the graphical switch element 34 from the first state to the different second state. Optionally, as explained above, the user, via the user interface 13, provides a user input switching the graphical switch element 34 from the first state to the second state.

In step S5, a contracting graphical element 31b is generated by the processor 11 as part of a second dynamic image, which second dynamic image is rendered on the display 14. In a preferred embodiment the contracting graphical element 31b is displayed for 2-20 seconds, preferably 7 seconds. The contracting graphical element 31b rendered on the display 14 may represent or invoke imagery associated with exiting a space filled with light. This has the effect of bringing the user's mind back from an inner focus in a controlled fashion and returning the user's attention to the outside world.

In an embodiment, a plurality of moving graphical elements 32b are generated and rendered, by the processor 11, on the display 14, as moving inwards (as is described in more detail with reference to FIG. 4b). In particular, the moving graphical elements 32b are generated as small or point-like moving graphical elements 32b which are rendered to move inwards towards a central region of the display 14. The inwardly moving graphical elements 32b have the effect of invoking movement, such that the user feels as though the user is moving away from the central region of the display 14 with the moving graphical elements 32b rushing past the user. Depending on the embodiment, the moving graphical elements 32b are generated and rendered prior to generating and rendering the contracting graphical element 31b, generated and rendered simultaneously with the expanding graphical element 31a as part of the second dynamic image, and/or generated and rendered subsequent to rendering the contracting graphical element 31b as described in step S5. In a preferred embodiment the statis image is rendered for 2-30 seconds, most preferably 11 seconds.

The graphical elements 31a, 31b, 32a, 32b, 33, 34, 35 described herein are generated by the processor 11 using program code and/or data stored in the memory 12. The program code and/or data may include video data, animation data, graphical object data, or other program code and/or data which enables the processor 11 to generate the graphical elements 31a, 31b, 32a, 32b, 33, 34, 35 disclosed herein.

The graphical elements 31a, 31b, 32a, 32b, 33, 34, 35 and the full-body user image 2 disclosed herein are rendered on the display 14 using the processor 11 and, in an example, a rendering pipeline.

The collection of steps described herein are for example performed in sequence, however certain steps can be exchanged or overlap with other steps, such that some graphical elements or visual effects can appear in another order than described or blend into each other.

The collection of steps described herein as being performed by the electronic treatment device 1 contribute to the technical therapeutic treatment effect of treating a psychological anxiety disorder, in particular by reducing a stress response related to a particular aspect of the phobia, fear, or source of stress. Scientific evidence of the effectiveness of treatment using the treatment device 1 is provided by the scientific study described herein.

The user can repeat the collection of steps described above as desired, until the particular aspect of the user's phobia, fear, or source of stress, is diminished. Afterwards, the user can repeat the collection of steps above, bearing in mind a different aspect of the user's phobia, fear, or source of stress, or alternatively addressing a further phobia, fear, or source of stress.

In another embodiment the aspect the user wishes to address can be selected from a predefined list of aspects or the user can define a new individual aspect, if the aspects provided do not contain the desired entry. This new individual aspect can be optionally stored in a user specific library of aspects, which can include both individual and predefined aspects allowing the user to create a list of aspects on which to focus.

The user can select if the selected aspect is displayed on the display permanently or if it removed, allowing the user to focus on the images shown on the display. This setting can be set globally for all aspects, for a user specific library or individually for each aspect.

Figure 3A:
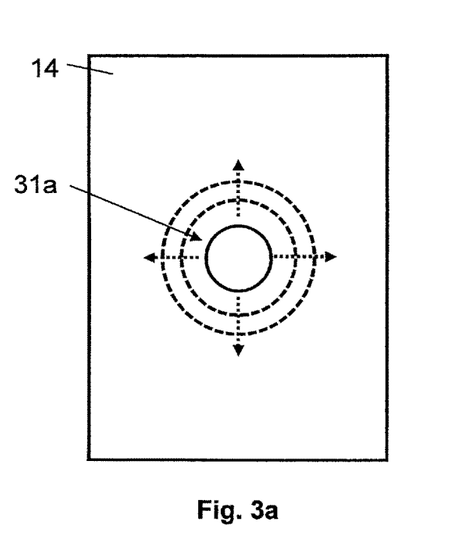
FIGS. 3a and 3b show illustration of a display showing an expanding, respectively contracting, graphical element on the display.
Figure 3B:
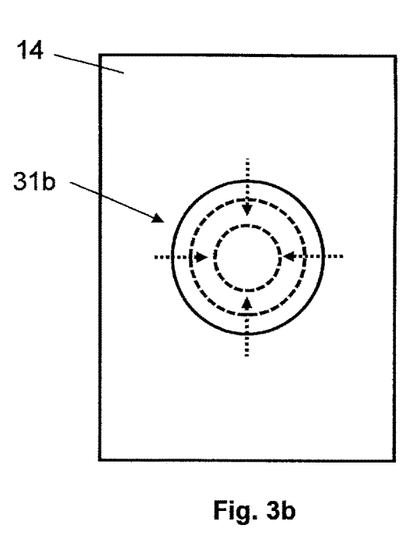

FIG. 3a shows an illustration of the expanding graphical element 31a. The expanding graphical element 31a for example has a light color and is rendered against a dark background. The expanding graphical element 31a is generated and rendered such that it appears initially small and roughly in the center of the display 14, and then expands over time to fill, or at least substantially, fill the entire display 14. For example, the rate of expansion of the expanding graphical element 31a is similar in all directions. For example, the expanding graphical element 31a is a white filled circle against a black background which is generated and rendered to expand from a small, or even point-like size to an ever increasing size such that over a pre-determined period it fills the entire display 14.

FIG. 3b shows an illustration of the contracting graphical element 31b. Similarly to the expanding graphical element 31a, the contracting graphical element 31b for example has a light color and is generated and rendered against a dark background. The contracting graphical element 31b is generated and rendered such that it is initially large and fills, or at least substantially fills, the display 14 and then is rendered such that it contracts towards the center region of the display 14. For example, the rate of contraction of the contracting graphical element 31b is similar in all directions. For example, the contracting graphical element 31b is a large white filled circle against a black background which contracts to a point-like size.

The colors of the expanding graphical element 31a and the contracting graphical element 31b, as well as other graphical elements disclosed herein, are non-limiting so long as a contrast against the background is achieved. Depending on the embodiment, therefore, the graphical elements 31a, 31b, 32a, 32b, 35 are white against a black background, yellow against a black background, etc. It can be beneficial to use complementary colors for creating a strong contrast.

In another embodiment an option is provided allowing the user to select the expanding and contracting graphical elements to be used according to personal preference or a recommendation by a treatment professional from a list with different options. Additional options can be provided to select the color, brightness, color-pace (color, gray scale, b/w) and for setting the time during which the expanding and contracting graphical elements are displayed.

Figure 4A:
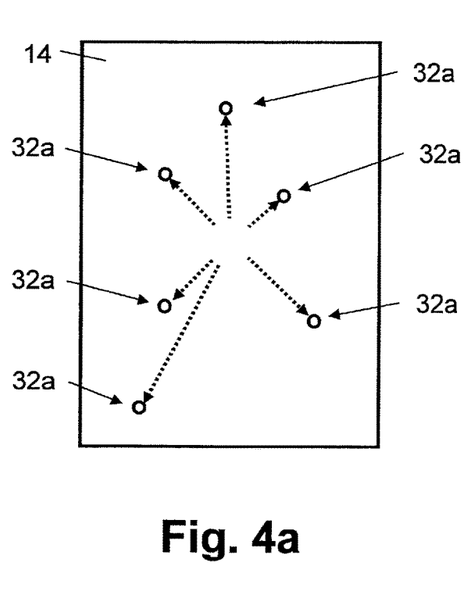
FIGS. 4a and 4b show illustration of a display showing outward, respectively inward, moving graphical elements.

FIG. 4a shows an illustration of the moving graphical elements 32a moving outwards from a central region of the display 14. The moving graphical elements 32a are light-colored against a dark background, e.g. white against a black background. The moving graphical elements 32a are generated and rendered to move to the edge of the display 14 and then disappear. In an example, additional moving graphical elements 32a are subsequently generated and rendered which appear at or near the central region of the display 14 and subsequently move outwards. For example, the moving graphical elements 32a are rendered as fuzzy balls of light.

Figure 4B:
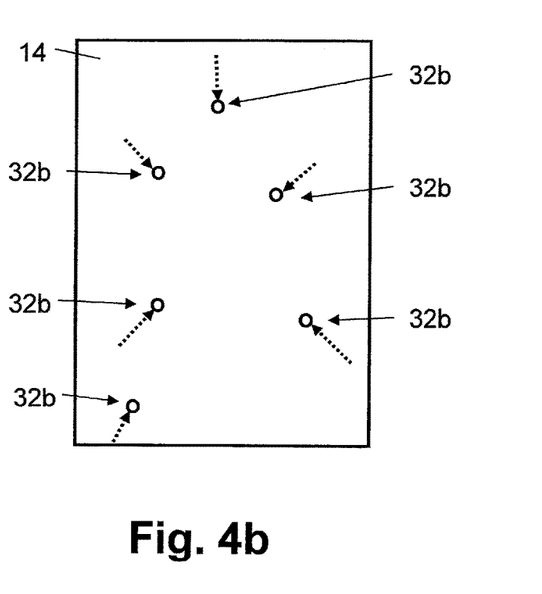

FIG. 4b shows an illustration of the moving graphical elements 32b generated such that the moving graphical elements 32b appear to move inwards towards the central region of the display 14. The moving graphical elements 32b are for example generated and rendered to appear at the edge of the display 14 and, move towards the center region of the display 14, and disappear.

FIG. 5a shows an illustration of the graphical turning element 33 turning from a first orientation to a second orientation. FIG. 5b shows the graphical turning element 33 in the second orientation. The processor 11 can be configured to turn the graphical turning element 33 automatically after a pre-determined time period, or to turn the graphical turning element 33 upon reception of a user input via the user interface 13.

FIG. 6a shows an illustration of the switch graphical element 34 in a first state. The switch graphical element 34 is switched from the first state to the second state by the processor 11. Optionally, the user switches the switch graphical element 34 from the first state to a second state (as depicted in FIG. 6b) via the user interface 13, for example using a swipe gesture on a touch-enabled display 14.

FIG. 7a shows an illustration of a full-body image 2 of the user rendered on the display 14. FIG. 7b shows the switch graphical element 34 rendered overlaid of the full-body image 2 in the first state, such that the switch graphical element 34 appears in front of the full-body image. FIG. 7c shows the switch graphical element 34 rendered overlaid of the full-body image 2 in the second state.

In another embodiment the displayed full body image 2 varies when the switch graphical element 34 is displayed in the first and second state. For example the brightness can be increased, or color and contrast can be gradually increased from the first to the second state.

Figure 8:
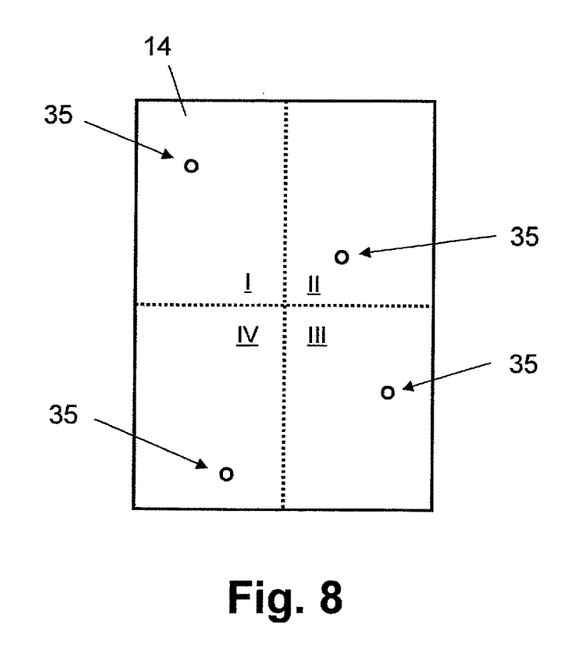
FIG. 8 shows an illustration of a display showing a plurality of graphical elements which appear in different quadrants of the display.

FIG. 8 shows an illustration of multiple point-like graphical elements 35. The processor 11 is configured to generate and render the point-like graphical elements 35 on the display 14 in a sequence, which is for example randomized, such that the point-like graphical elements 35 appear one after another in random positions on the display 14. For example, the sequence is configured such that at least one point-like graphical element 35 appears in the left half of the display 14 and in the right half, more for example each quadrant (I, II, III, IV) of the display. The user, by looking at the point-like graphical elements 35 as the point-like graphical elements 35 appear, will focus his eyes to the left and also to the right. This results in an increased communication between both brain hemispheres and has been shown to reduce the vividness and emotion associated with phobia and fear, in particular by reducing activity in the vagus nerve.

The point-like graphical elements 35 are for example generated and rendered in a step subsequent to step S5. In addition an image, for example a nature photograph, can be rendered before or after the point-like graphical elements.

The duration for which the point-like graphical elements 35 are shown is selected depending on the embodiment, but is is preferably between 0.5 seconds and 5 seconds.

Figure 9:
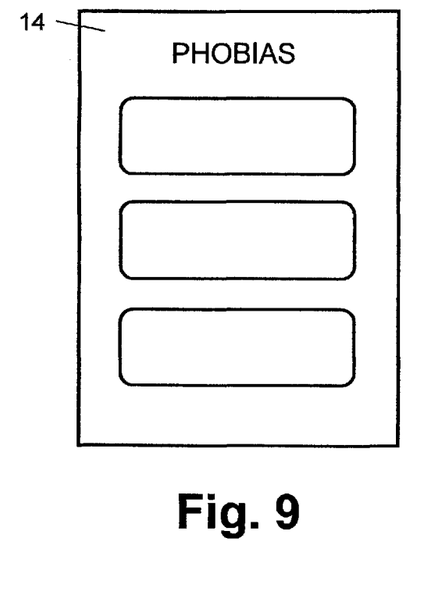
FIG. 9 shows a block diagram of a display showing a plurality of phobias and fears.

FIG. 9 shows an illustration of the display 14 rendering a list of phobias, fears and/or sources of stress. The user selects a particular phobia, fear, or stress prior to the treatment, using the user interface 13. For example, the list of phobias includes arachnophobia and the fear of heights.

Figure 10:
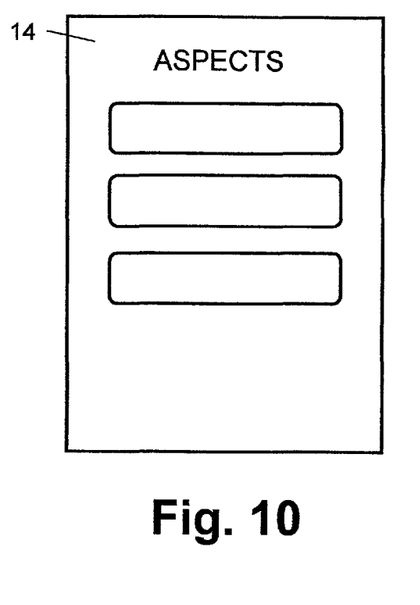
FIG. 10 shows a block diagram of a display showing a plurality of aspects of a particular phobia and fear.

FIG. 10 shows an illustration of the display 14 rendering a list of aspects of the particular phobia, fear, or source of stress which the user selected. For example, if arachnophobia was previously selected, the list of aspects includes aspects such as: disgust, that the spider is monstrous, that the spider has many legs, that the spider has sudden and jerky movements, that the spider has a penetrating gaze. The user selects a particular aspect using the user interface 13.

Figure 11:
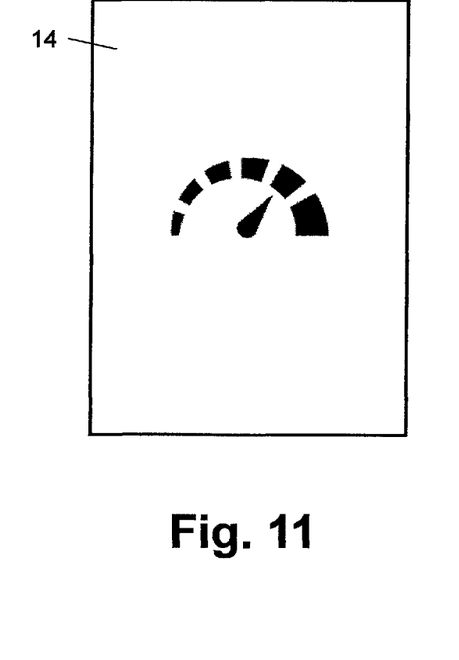
FIG. 11 shows a block diagram of a display illustrating a user selectable stress value.

FIG. 11 shows an illustration of a stress level control. The user, prior to and subsequent to treatment, inputs a current stress level associated with the user's phobia or fear. For example, the user selects a stress level on a scale between 0 and 10, using the user interface 13. The processor 11 is configured to evaluate and record a difference between the current stress level subsequent to and prior to treatment and store the results as a user history in a memory. For example, for a subsequent treatment, the processor may select a sequence of images or a duration of each image based on the user history taken into consideration the information related to the previous treatments and reduction of stress.

In an embodiment the user can add a personal note in addition to selecting the stress level. In a future session with a treatment professional these notes can be used to review the progress and address existing or new issues.

In a further embodiment a treatment session consists of several rounds of steps S1 to S5 shown in FIG. 2. After each round the user is prompted to decide from the following options: repeat the steps for the same aspect, create and select a new individual aspect, select a different aspect from the current list of aspects, or end the treatment session.

The above-described embodiments of the disclosure are exemplary and the person skilled in the art knows that at least some of the components and/or steps described in the embodiments above may be rearranged, omitted, or introduced into other embodiments without deviating from the scope of the present disclosure.

Scientific Study

The following section relates to the results of the scientific study performed and is included to provide evidence of the effectiveness of the treatment provided by the disclosed electronic treatment device.

The electronic treatment device used during the study used a particular set of durations for displaying the image which are detailed below. Additional settings were used outside of the study showing that at least some of these parameters may be set differently without significantly changing the outcome of the treatment. In particular, the first dynamic image comprising the expanding graphical element 31a (in step S1) was displayed for 11 seconds. The graphical turning element was displayed for 5 seconds with a 3 second pause before the full-body image 2 was displayed for 10 seconds. Six seconds later after the rendering the full-body image 2 had started, the graphical switch element 34 was rendered on the display 14 for 4 seconds and then disappeared together with the full-body image 2. The second dynamic image was rendered for 7 seconds, then after a 7 second pause, the plurality of moving graphical elements 32b were rendered for 11 seconds.

Functional magnetic resonance imaging (fMRI) is used to measure activities in the brain via changes in metabolism. The basic principle is based on phenomena in the magnetic field. When a brain region is working hard, it consumes energy, which means that fresh oxygen must be transported to these regions with the help of the blood. This change is measured. This signal is called the BOLD effect (blood-oxygen-level-dependent). This contrast is dependent on the oxygen content in the red blood cells. Red blood cells that have released their oxygen act like small iron molecules, i.e. small magnets that disturb the magnetic field. The magnetic resonance signal measures a weaker signal in this area.

This method is primarily based on the question of which brain regions are more or less involved in certain processes, or where in the brain something happens. The great advantage of the method is that brain activities can be localized very precisely.

The MRI device used was a Siemens Magnetom Prisma 3 Tesla MRT with 64 resp. 20 Channel head coil. fMRI data was as follows: T2* weighted GE-EPI SMS sequence, TR 1050 ms, 2.4×2.4×2.4 mm voxel. The data preprocessing and statistical analyses are done by means of SPM12 (http://www.fil.ion.ucl.ac.uk/spm) and in-house Matlab scripts. For preprocessing head movements are corrected and the functional data are entered into the MNI Standard space normalized and spatially smoothed (6 mm FWHM).

Twelve physically healthy subjects with arachnophobia (7 women, 5 men between 22 and 65 years of age—average age: 33.08 years) were recruited. None of the subjects was undergoing psychological treatment for spider phobia at the time of the study.

Subjects were exposed to 25 images of spiders, as well as 25 control images of animals (repeated and randomized) in a magnetic resonance imaging scanner. After the first scan, the treatment as disclosed herein was used for an average of 100 minutes per subject. During this application, there were no conversations, no distractions, and no other activities. After treatment, subjects were repeatedly presented with the image set of 25 spider and 25 control images while their neural processing in the brain was measured.

Figure 12A:
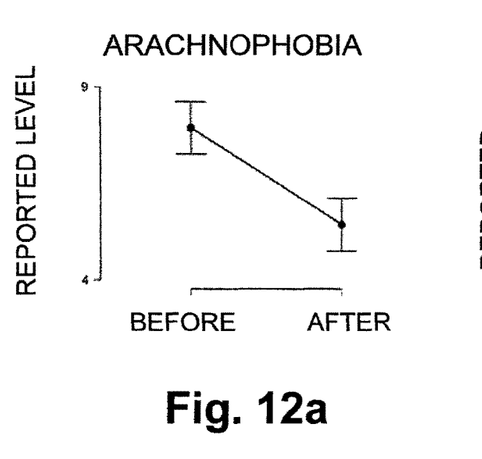
FIGS. 12a and 12b show two charts indicating user reported levels of fear before and after treatment, as reported in the study.
Figure 12B:
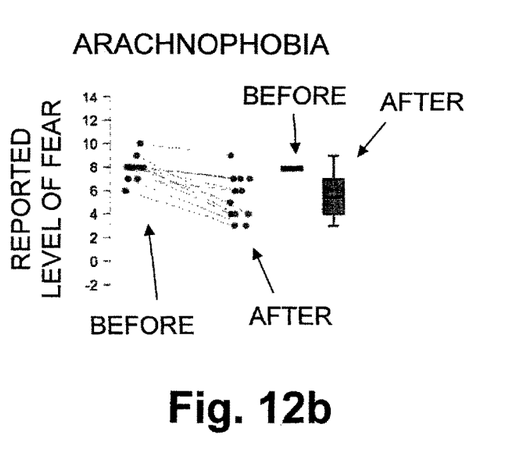

After using the application, there was a statistically significant reduction in reported spider anxiety by an average of 2.5 units among the 12 experimental participants, see FIG. 12a (mean of reported spider anxiety before using the application 7.92, mean after using the application 5.42; $t(11)=5.745$, $p<0.001$). This reduced the reported mean spider anxiety by 31.57%. As shown in FIG. 12b, there was a numerical reduction in reported spider anxiety after using the application in each of the 12 experimental participants, although this individual reduction varied in magnitude.

To study brain activity using functional MRI, it was first focused on a region-based analysis for the left and right amygdala, as these two regions are strongly implicated in feelings of fear and anxiety (Costafreda et al., 2008; Tao et al., 2021) and have been identified as important brain regions in a number of studies on phobia and its successful treatment (Ipser et al., 2013; Penate et al., 2017). Brain activity was calculated during viewing images of spiders compared to a control condition in which images of other animals that are not fear-inducing were viewed. Hereafter, this differential activity will be referred to as spider-specific activity; it should be noted that differential activity is reported in arbitrary units because fMRI studies with BOLD contrast are not measures with defined units. Both left and right amygdala showed a numerically pronounced reduction in spider-specific activity after, compared with before application use from a mean activity of 7.34 to 2.23 for the left and from 6.41 to 0.69 for the right amygdala. This corresponds to a strong reduction in mean activity of 69.48% for the left amygdala and 89.55% for the right amygdala after application use.

Figure 13:
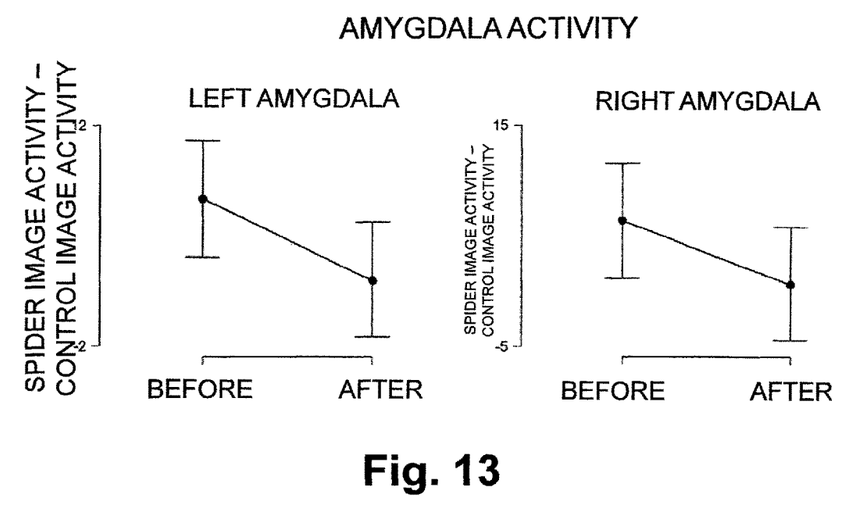
FIG. 13 shows two charts indicating measured levels of amygdala activity before and after treatment.
Figure 14:
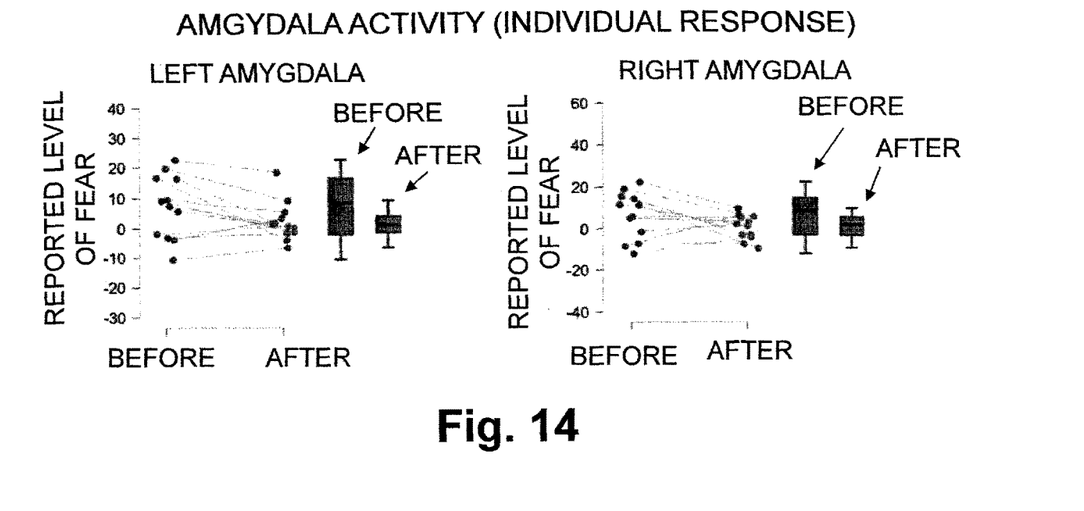
FIG. 14 shows two charts indicating individual measured levels of amygdala activity before and after treatment.

Statistically significant was the reduction in spider-specific activity (detected by one-sided paired-sample t-tests based on the expected reduction in activity after application use) in the left amygdala ($t(11)=2.17$, $p=0.026$, in the right amygdala the reduction just did not reach the statistical significance threshold ($t(11)=1.73$, $p=0.056$). Individually, numerical reduction (see FIGS. 13 and 14) was evident in 8 of 12 participants in the left amygdala and in 9 of 12 participants in the right amygdala. Considered together, 9 of 12 participants showed a numerical reduction in spider-specific brain activity in either the right and/or left amygdala after using the application.

Figure 15:
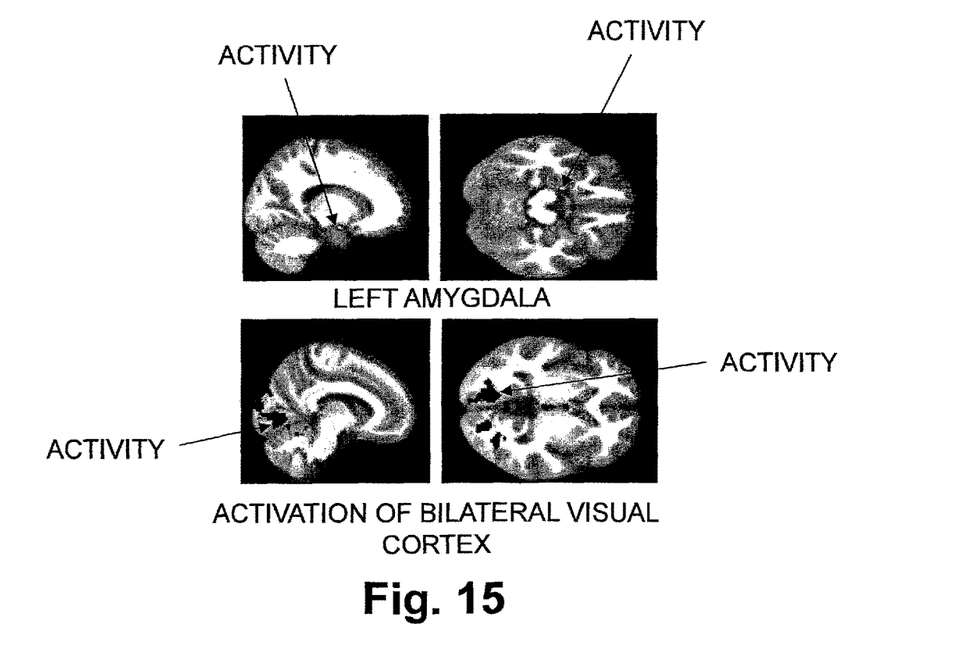
FIG. 15 shows FMRI images of the left amygdala and the bilateral visual cortex.
Figure 16:
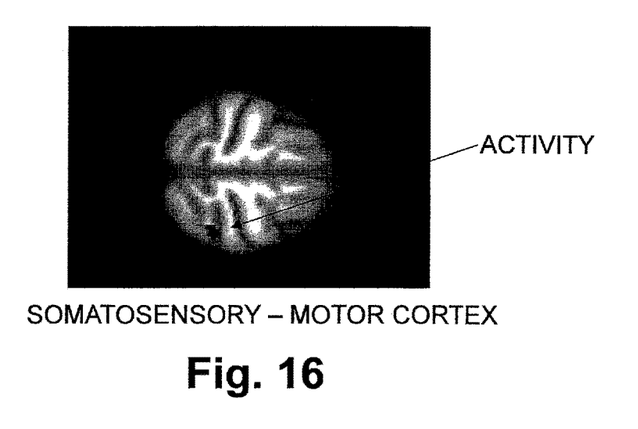
FIG. 16 shows an FMRI image of the somatosensory—motor cortex.

To investigate whether additional brain regions showed a statistically significant reduction in spider-specific brain activity after application use, a statistical comparison was calculated using a paired-sample t-test voxel-based across the entire brain. FIGS. 15 and 16 show which regions showed a statistically significant reduction of activity after application use compared to before application use: the left amygdala (FIG. 15, top images), the bilateral visual cortex (FIG. 15, bottom images) and also a region in the somatosensory cortex (FIG. 16). Activity is shown as black pixels, as indicated in the Figures.

A more detailed analysis of these changes in spider-specific activity in these regions was conducted below. Since the analysis described above already established the statistical significance of this region was established, no further significance tests were performed for this analysis.

Figure 17A:
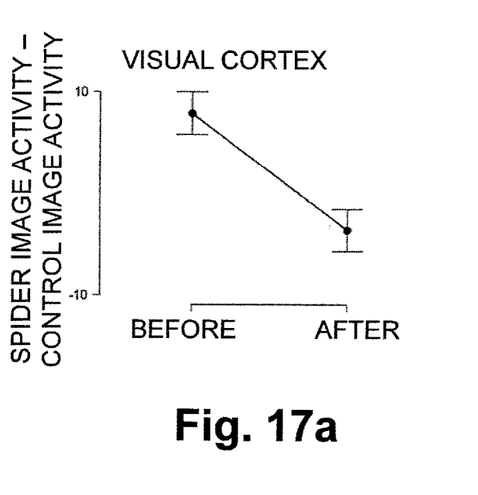
FIGS. 17a and 17b show two charts indicating measured levels of activity in the visual cortex before and after treatment.
Figure 17B:
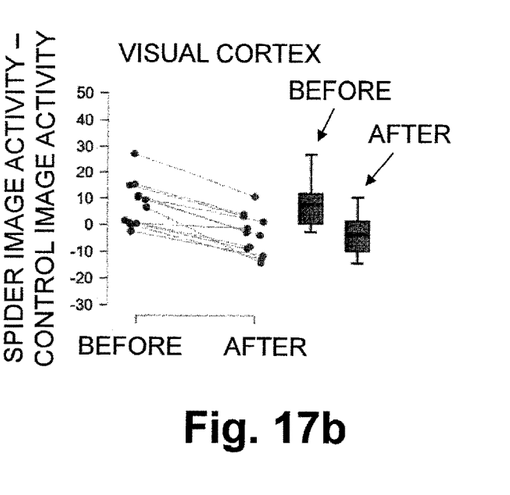

There was a reduction in spider-specific activity in these visual regions from an average of 7.9 to an average of −3.7 units, corresponding to a reduction in spider-specific activity after using the application of 146.84% (more than 100% since activity before application was stronger for spider images than control images and showed the opposite effect after using the app). Individually, each experimental participant showed a numerical reduction in activity in this visual cortex region after using the application (see FIGS. 17a and 17b).

Figure 18A:
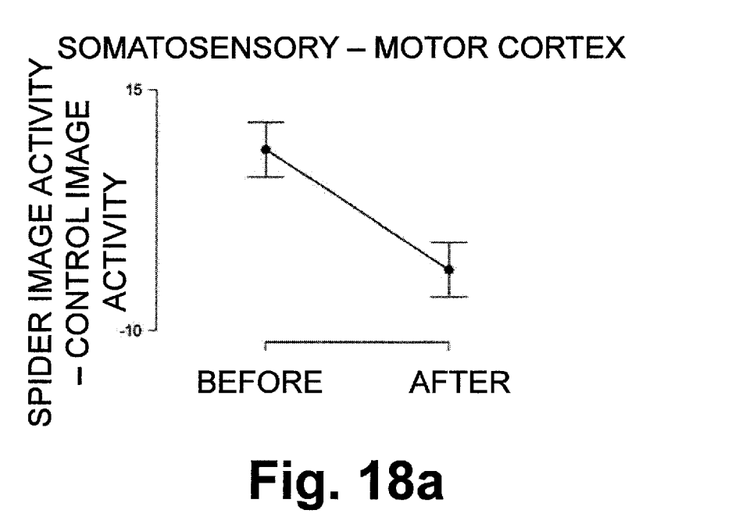
FIGS. 18a and 18b show two charts indicating measured levels of activity in the somatosensory-motor cortex before and after treatment.
Figure 18B:
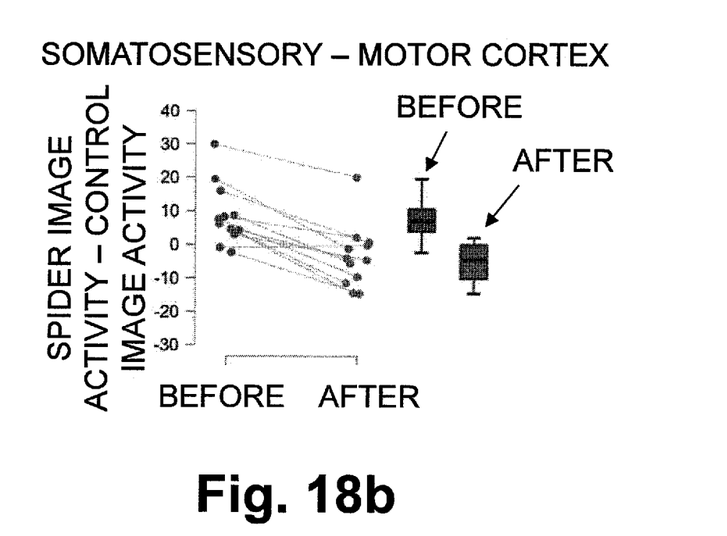

In the right somatosensory-motor cortex, there was a reduction from a mean activity of 8.7 to a mean activity of −3.64 units, corresponding to a reduction of the mean spider-specific activity after using the application by 141.84% (more than 100% since the activity before application was stronger for spider images than control images and showed the opposite effect after using the app). Individually, 11 of 12 participants showed numerically reduced activity after using the application (see FIGS. 18a, 18b).

A strong reduction of spider fear in the brain after a single application of treatment using the electronic treatment device (100 minutes) could be demonstrated: In the left amygdala, the average activity was reduced by 69.48%, in the right by 89.55%. In the visual regions of the brain there was a reduction from an average of 7.9 to an average of −3.7 units, and in the somatosensory-motor cortex there was a reduction in mean activity from 8.7 to a mean activity of 3.63 units.

To better understand the efficacy of the electronic treatment device 1 during the study, a single application of 100 minutes was used. However, it is not necessary or required to perform a treatment session of such a duration to achieve a reduction in stress. The user can use the electronic treatment device 1 to perform treatment on demand, achieving a reduction in stress when it is most easily arranged or desired.

Further, as the user may become aware of further aspects of the user's phobia, fear, or stress, these further aspects can be treated individually in subsequent treatment sessions which can lead to a further reduction in stress of the overall phobia, fear, or source of stress.

While certain embodiments have been particularly shown and described with reference to the drawings, embodiments are provided for the purposes of illustration and it will be understood by one of ordinary skill in the art that various modifications and equivalent other embodiments may be made from the disclosure. Accordingly, the true technical scope of the disclosure is defined by the technical spirit of the appended claims.

The invention claimed is:

1. An electronic apparatus configured to provide a treatment for a psychological anxiety disorder, the electronic apparatus comprising:
a memory storing at least one instruction;
a user interface comprising a display configured to display a plurality of images; and a processor which is, by executing the at least one instruction, configured to: based on a first user input received through the user interface, generate a first dynamic image comprising an expanding graphical element among the plurality of images, and render the first dynamic image on the display such that an expansion is centered on a point located in a central region of the display, generate a graphical turning element which is rendered on the display in a first state and subsequently rendered on the display in a second state different from the first state, among the plurality of images, render, on the display, a full-body image of a user in a pre-defined orientation, a predefined location, and a pre-defined size, among the plurality of images, generate a graphical switch element which is rendered on the display in a first state and subsequently rendered on the display in a different second state, among the plurality of images and generate a second dynamic image comprising a contracting graphical element among the plurality of images, and render the second dynamic image on the display such that a contraction is centered on the point located in the central region of the display, wherein the processor is further configured to: receive, through the user interface, the first user input comprising an indication of a first stress level of the user, prior to rendering the first dynamic image, receive, through the user interface, a second user input comprising an indication of a second stress level of the user, subsequent to rendering the second dynamic image, and determine whether the stress level of the user has been reduced by comparing the second stress level to the first stress level.

2. The electronic apparatus of claim 1, wherein the first dynamic image comprises one or more first moving graphical elements, wherein each of the one or more first moving graphical elements moves outwards from the point located in the central region of the display.

3. The electronic apparatus of claim 1, wherein the second dynamic image comprises one or more second moving graphical elements, wherein each of the one or more second moving graphical elements moves toward the point located in the central region of the display.

4. The electronic apparatus of claim 2 or 3, wherein at least one from among the first dynamic image and the second dynamic image is generated to have a black background, and at least one from among the expanding graphical element and the contracting graphical element is generated to have a white color.

5. The electronic apparatus of claim 1, wherein the processor is further configured to perform image processing on the full-body image of the user, and render the full-body image of the user as a desaturated full-body image, and wherein the desaturated full-body image has a size in a lengthwise direction between 3 cm and 8 cm.

6. The electronic apparatus of claim 1, wherein the full-body image of the user is rendered as a partially transparent full-body image.

7. The electronic apparatus of any one of claims 1, 2, 3, 4 or 5, wherein the processor is further configured to render at least one from among the graphical switch element and the graphical turning element to be overlaid on the full-body image.

8. The electronic apparatus of any one of claims 1, 2, 3, 4 or 5, wherein the processor is further configured to generate and render at least one from among the full-body image, the graphical turning element, and the graphical switch element, such that at least one from among the full-body image, the graphical turning element, and the graphical switch element is rendered for a predetermined period of time and then fade, at a pre-determined fade rate.

9. The electronic apparatus of claim 1, wherein the processor is further configured to generate the second state of the graphical turning element, wherein, in the second state, the graphical turning element is rotated from the first state by 180°.

10. The electronic apparatus of claim 1, wherein the first user input comprises an indication of one or more types of psychological anxiety disorder.

11. The electronic apparatus of claim 1, further comprising a speaker, wherein the processor is further configured to play back one or more audio tracks associated with the plurality of images, the one or more audio tracks conveying instructions to the user.

12. The electronic apparatus of claim 1, wherein the electronic apparatus is a portable communication device comprising at least one from among a smart phone, a tablet computer, a smart watch, and a laptop.

13. The electronic apparatus of claim 1, wherein the display of the user interface comprises at least one from among an augmented reality display and a virtual reality display.

* * * * *